United States Patent [19]

Compos

[11] Patent Number: 4,823,800
[45] Date of Patent: Apr. 25, 1989

[54] IMPLANTABLE ULTRASONIC PROBE AND METHOD OF MANUFACTURING THE SAME

[75] Inventor: Andre C. Compos, Pantin, France

[73] Assignee: Virbac, a French Corporation, Carros, France

[21] Appl. No.: 895,428

[22] Filed: Aug. 11, 1986

[30] Foreign Application Priority Data

Aug. 12, 1985 [FR] France .............................. 85 12297

[51] Int. Cl.⁴ ............................................. A61B 10/00
[52] U.S. Cl. .................................. 128/661.08; 73/644
[58] Field of Search ............................... 128/660–663; 73/622–644, 861.25

[56] References Cited

U.S. PATENT DOCUMENTS

| | | | |
|---|---|---|---|
| 3,661,146 | 5/1972 | Peronneau et al. ................. | 128/663 |
| 3,827,115 | 8/1974 | Bom ..................................... | 128/661 |
| 3,938,502 | 2/1976 | Bom ..................................... | 128/661 |
| 4,168,628 | 9/1979 | Villcomerson ................. | 128/660 X |
| 4,205,686 | 6/1980 | Harris et al. ......................... | 128/660 |
| 4,327,738 | 5/1982 | Green et al. ......................... | 128/660 |
| 4,355,643 | 10/1982 | Laughlin et al. .................... | 128/663 |
| 4,413,629 | 11/1983 | Durley, III .......................... | 128/660 |
| 4,446,395 | 5/1984 | Hadjicostis ......................... | 128/660 |
| 4,459,854 | 7/1984 | Richardson et al. ............ | 128/661 X |
| 4,503,861 | 3/1985 | Entrekin ............................. | 128/661 |
| 4,532,933 | 8/1985 | Hohanson .......................... | 128/660 |
| 4,541,433 | 9/1985 | Baudino ............................. | 128/668 |

FOREIGN PATENT DOCUMENTS

| | | | |
|---|---|---|---|
| 0092080 | 10/1983 | European Pat. Off. . | |
| 1574194 | 7/1969 | France ................................. | 128/660 |
| 1601372 | 9/1970 | France ................................. | 128/660 |
| 2173115 | 10/1973 | France . | |
| 2352286 | 12/1977 | France ................................. | 128/660 |
| 2461486 | 2/1981 | France ................................. | 128/660 |
| 2507075 | 12/1982 | France ................................. | 128/660 |
| 2543817 | 10/1984 | France . | |
| 14021928 | 8/1975 | United Kingdom . | |

OTHER PUBLICATIONS

Search Report of European patent application (Nov. 25, 1986).
J. Knutti et al., "Clinical Application of the Pulsed Doppler Ultrasonic Blood Flowmeter," *Wescon Technical Papers*, vol. 19, pp. 1–9 (1975).
Wells, P. N. T., "Biomedical Ultrasonics," Academic Press, N.Y., 1977, pp. 57–58.

*Primary Examiner*—Francis J. Jaworski
*Attorney, Agent, or Firm*—Mason, Fenwick & Lawrence

[57] ABSTRACT

An ultrasonic probe is adapted to be implanted in a human or animal body in contact with a wall of an organ to allow exploration of the organ by ultrasonics, inter alia by the Doppler effect. It comprises a support for a piezo-electric transmitter/receiver transducer, and a cover which covers the transducer and at least that part of the support which is remote from the organ. The transmitting/receiving surface of the transducer is in contact with a surface of the support, which is interposed between the transducer means and the organ. The probe also has conductors attached to the transducer extending to the outside of the body to carry the information transmitted/received by the probe. The support and the cover have a configuration and shape such as to allow the probe to be removed from the body without a complex surgical operation, particularly by simply pulling from outside on the connecting means.

25 Claims, 2 Drawing Sheets

IMPLANTABLE ULTRASONIC PROBE AND METHOD OF MANUFACTURING THE SAME

BACKGROUND TO THE INVENTION

1. Field of Invention

This invention relates to an ultrasonic probe which is adapted to be implanted in a human or animal body and a method of manufacturing the same.

The invention is suitable for the ultrasonic exploration of an organ, in contact with which it is applied, for example by measuring the velocity of the blood inside a blood vessel, such as the aorta, by the Doppler effect. The invention also enables the diameter of the blood vessel to be measured, so that its cross-section can be calculated. It will also be possible in this way to calculate the rate of flow of the blood inside the vessel. However, the invvention can be used in other areas of industry for measuring speeds and rates of flow of fluids by the Doppler effect, or for exploring organs other than a blood vessel and other than by the Doppler effect (e.g. for measuring the thickness of cardiac walls etc.).

2. Description of Prior Art

Doppler effect ultrasonic perivascular probes are known. These probes emit an ultrasonic acoustic wave in a fluid which reflects such a wave. The reflected signal received by the probe has a slightly different frequency from that of the transmitted wave, and this difference is a function of the speed of the fluid. The known perivascular probes have piezo-electric transmitter/receiver means connected electrically to external apparatus providing the power and transmission signal, for analyzing the reflected signal, and so on. These latter external items of apparatus do not form part of the invention.

French Pat. No. 1 601 372 describes a piezo-electric type pick-up intended for measuring blood velocity in order to calculate the rate of blood flow, by ultrasonic probing in which one of the surfaces of the piezo-electric ceramic plate not facing the propagation medium is in contact with a mass of material, inter alia rubber, foam or resin with fillers, to provide acoustic decoupling from the propagation medium. A pick-up of this kind may be fixed to the end of the catheter, or inserted in a cap of the perivascular type. In the latter case, fixing to the vessel is provided by a strip of Dacron (Registered Trade Mark), and a gel mass disposed on the transmitting surface of the plate to match the impedance to the vascular wall. The resulting probe is mainly made of Altuglas (Registered Trade Mark) or some other material which is conventionally transparent to ultrasound.

A known probe of this kind does not offer all the properties, inter alia sealing properties, which allow its long-term implantation in a living organism.

French Pat. No. 1 574 194 also describes a Doppler effect perivascular probe in which each transducer is embedded within a support and its surface remote from the support and intended for application against the medium under examination, is covered with a layer of material having a high acoustic impedance. However, this known probe is not adapted to long-term implantation in a living organism.

French Pat. No. FR 2 352 286 relates to a Doppler effect perivascular probe in which the devices which allow its operation are integrally implantable, and which can be controlled from outside the organism electromagnetically. A probe of this kind is difficult to use in practice because the system is too bulky for long-term implantation in a living organism and requires an implanted power source which requires periodic replacement. Also, its removal necessitates a complex, delicate and expensive surgical operation.

In a first embodiment of the known perivascular probes they are provided with a piezo-electric transmitter element and a piezo-electric receiving element. In that case the ultrasonic wave transmission is continuous. In a second embodiment of these probes, they operate by the pulsed Doppler effect. In that case, the ultrasonic waves are emitted with an intermittent pulsed transmission. Only a single piezo-electric transmitter/receiver element is then used. Transmission is carried on for some time, then interrupted, and followed by the reception of the reflected signals. The frequency of the transmission/sound reception cycles is calculated according to the depth to be explored i.e. the vessel diameter.

In order to ascertain the depth to be explored and the velocity of the blood (or other fluid), the probe is applied to the wall of the organ and then ultrasonic waves are transmitted at an ever-increasing exploratory distance. Where these waves do not penetrate to the interior of the vessel, they are reflected by fixed obstacles and no frequency variation is found. The range of the exploratory distances at which frequency variation is observed thus enables the inside diameter of the blood vessel to be determined differentially. In this case it will be seen that the accuracy with which the probe is applied to the organ is important, for if it is not perfectly centered the measured exploration depth will not correspond to the real diameter of the vessel.

To measure the velocity of the blood in a blood vessel by means of such Doppler effect ultrasonic perivascular probes, the probe must be applied to the organ under investigation whenever a measurement is to be taken. The probe is removed at the end of the measurement. The inventor has found that these probe manipulations are inconvenient, tedious and relatively time-consuming. Also, the piezo-electric discs used in such probes are thin (the thickness is of the order of a few tenths of a millimeter) and hence relatively weak. Probe handling must therefore be avoided to the maximum in order to prevent damage to the piezo-electric discs.

Numerous types of endoscopic probes are also known (French patent application Nos. 2 461 486, 2 507 075, 2 543 817 etc.). These probes are not intended for application in contact with an organ under examination. They do not therefore have to be implantable or removable. Also, these probes cannot be applied to measuring rate of flow by the Doppler effect. The invention on the other hand does not relate to the technical area of endoscopic probes for which the problems arising and the means used differ from those of probes applied directly against the organ wall under examination.

SUMMARY OF THE INVENTION

This invention obviates these disadvantages by proposing an ultrasonic probe which can be implanted in the human or animal body and which is intended to be applied in contact with a wall of an organ under examination.

In the context of the invention, a probe is said to be implantable when it can be applied against a wall of an organ for exploration inside the human or animal body and be left applied inside said body for as long as desired, or at least for a period of time far in excess of the duration of examination by said probe, without resulting in any rejection phenomena or other trauma in said body.

However, there are a number of problems in connection with the construction of such an implantable probe, inter alia as follows:

The choice of an implantable material which is transparent to ultrasound. The known implantable materials in fact are generally opaque to ultrasound.

Sealing and electrical insulation, because to be implantable a probe must be perfectly sealed and insulated electrically and the surrounding fluids must never be able to penetrate inside the probe, even in the long term, and cause damage such as short circuits, leakage of electrical current, corrosion, and so on.

Removal of the probe must be easily achieved.

The probe must be small. The ultrasonic waves must be transmitted and received at a certain angle of incidence in the fluid, and this means that the piezo-electric transmitter/receiver means must be inclined with respect to the direction of movement of said fluid, conventionally 45° in known Doppler effect probes. This phenomenon implies minimum height dimensions of the probe.

The problem of the acoustic coupling of the transmitter/receiver means with said material must be addressed.

The problem is in fixing the probe in position, because the probe must not be capable of shifting and must remain perfectly centered with respect to the organ, particularly in the case of a vessel.

The object of the invention is to obviate the above disadvantages, and to this end it proposes an ultrasonic transmitter/receiver probe adapted to be implanted in the human or animal body, of the type intended for application in contact with a wall of an organ to allow exploration inside the organ by ultrasound—using the Doppler effect—of the type comprising support means for piezo-electric transmitter/receiver transducer means, and a cover which covers the transmitter/receiver means and at least that part of the support means which is remote from the organ, the transmitting/receiving surface of the transmitter/receiver means being associated in contact with a surface of the support means which is interposed between the transmitter/receiver means and the organ, the probe also comprising means for connection with the outside of the body to carry the information transmitted/received by/on the probe, characterized in that the support means and the cover have a configuration and shape such as to allow the probe to be removed from the body without a complex surgical operation, that is simply by pulling from the outside on the connecting means. The support means has an outer surface for application to the organ wall and is formed from an implantable material which is a good conductor of ultrasound, such as a silicone elastomer without fillers. The cover is formed from an implantable material which is opaque to ultrasound, such as a silicone elastomer with fillers. The probe according to the invention has sealing and insulating means which provide complete sealing and electrical insulation of the probe with respect to the surrounding fluids. The outer surface of the cover is polished and substantially drop-shaped. The probe according to the invention has means for rigidly associating it with the organ under exploration, acoustic impedance matching means between the transmitter/receiver means and the support means, and means for protecting the transmitter/receiver means from the support means.

A probe of this kind is therefore readily implantable on an animal or human being and can be applied, for example, to the repeated measurement of the velocity of the blood and hence the rate of blood flow in a vessel (a vein, artery or the like) of the animal or human being as required. A probe of this kind can also be implanted in patients whose rate of blood flow must be taken uniformly, e.g. in order to follow cardio-vascular problems or diseases, or the like. Another application of the invention may be measuring the thickness of a wall.

It should also be noted that the inventor has discovered inter alia that not only silicone elastomers without fillers are good ultrasonic conductors, but also that the speed of the ultrasound is lower in these silicone elastomers than in the materials used for the manufacture of known probes, such as Plexiglas (Registered Trade Mark) or Altuglas (Registered Trade Mark). The transmitter/receiver means of a probe according to the invention are therefore inclined at a lesser angle to the direction of propogation of the fluid, so that their height can be reduced.

The invention also relates to a method of manufacturing a probe of this kind, in which the support means is manufactured inter alia by cutting or moulding of a block of silicone elastomer, giving it the appropriate shape, and then associating it rigidly, inter alia by gluing, with the piezo-electric transmitter/receiver means after it has been soldered to the output cable, whereupon the characteristics of the probe are tested (inter alia the frequency is measured), and when provided the protection means are fitted, followed by a cover to cover the transmitter/receiver means, the connection to the output cable the corresponding end of said cable, and the support means except for the outer surface for application to the organ under exploration, and when they are provided the sealing and/or electrical insulation means are fitted.

The invention will be more readily understood from the following description of one embodiment of a Doppler effect ultrasound probe for measuring rate of flow, this embodiment being given by way of example without any limiting force and with reference to the accompanying drawings.

DESCRIPTION OF PREFERRED EMBODIMENTS

Figure 1:
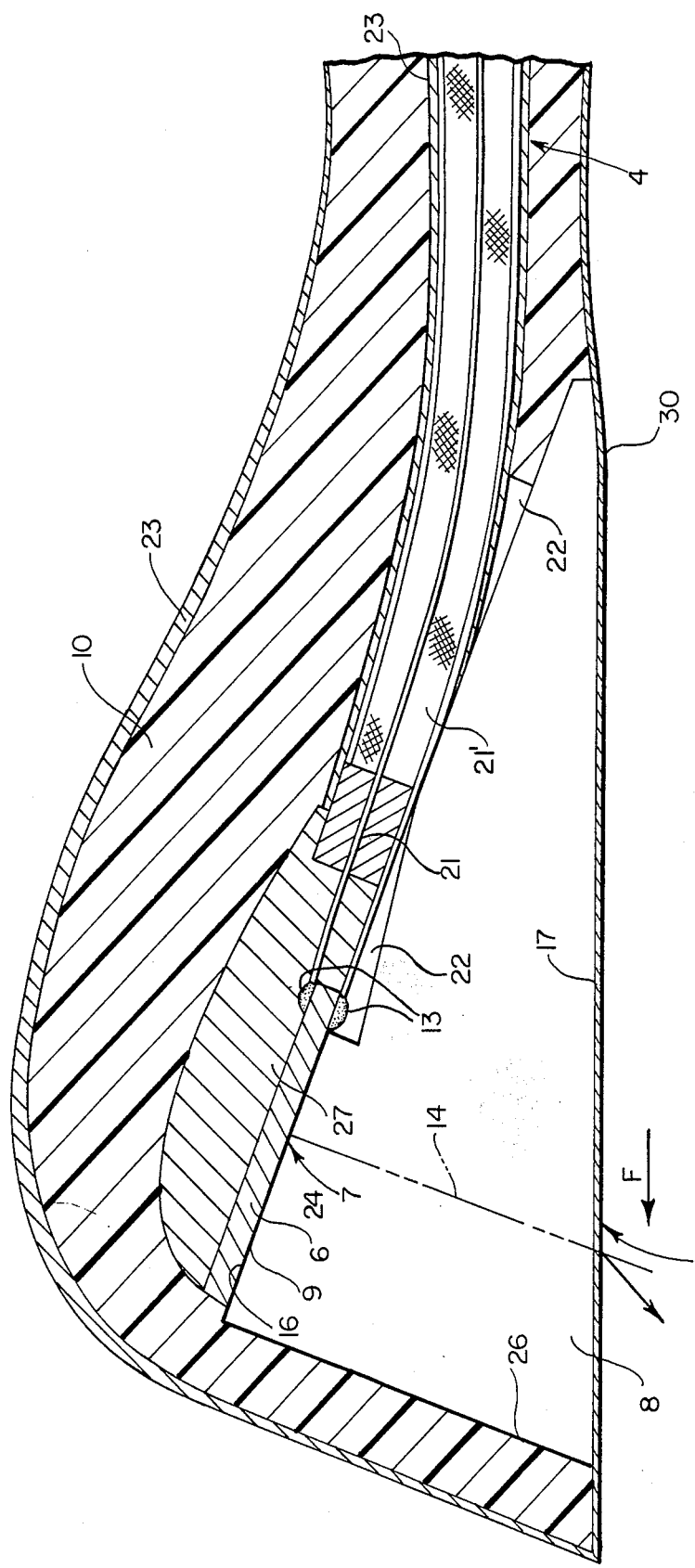
FIG. 1 is a diagrammatic side elevation of a probe according to the invention.

An ultrasound probe 1 comprises means 2 for investigation of the organ which it is required to explore, and means 3 for electrical connection with the exterior.

The connecting means 3 comprise an output cable 4 having an electrical connecting socket at the end remote from the probe, so that the probe can be connected to external apparatus (a power supply, analyzer means, etc.) not shown.

The investigation means 2 comprise in known manner piezo-electric transducer means 6 which transmit/receive ultrasonic waves. This transmitter/receiver transducer means 6 is generally in the form of a disc, the dimensions of which vary with the natural frequency required, and is connected electrically to the cable 4. One surface of the disc forms a useful transmitter/receiver surface 7 for the piezo-electric transmitter/receiver means 6, via which the ultrasonic waves, which allow the organ to be explored, are transmitted/received. The piezo-electric transmitter/receiver transducer means 6 converts the electrical energy into ultrasonic waves which it transmits and, conversely, converts the ultrasonic waves it receives into electrical current.

A probe 1 according to the invention comprises support means 8 made of an implantable material which is a good conductor of ultrasound. This material is preferably a silicone elastomer without fillers, which has been found to be a good conductor of ultrasound. The said piezo-electric transmitter/receiver means 6 overlies the support means 8. The transmitter/receiver surface 7 of said transmitter/receiver means 6 is in contact with upper surface 16 of the support means 8 by a rigid association means 9. A covering 10 of an implantable material which is opaque to ultrasound encases at least that part 11 of the support means 8 which is remote from the organ 15 being explored, and the transmitter/receiver means 6, and the end of the cable to which the transmitter/receiver means 6 are connected, and the connection 13 between the cable 4 and the transmitter/receiver means 6. The covering 10 does not extend over outer surface 17 of support means 8.

A part of the probe 1 according to the invention comprises sealing means providing complete sealing of the probe 1 with respect to the surrounding fluids, without interfering with its mechanical and acoustic characteristics, and electrical insulation means providing electrical insulation of the leads the connection 13, and the piezo-electric disc forming the transmitter/receiver transducer means 6 with respect to the exterior.

The function of the covering 10 is to form a screen which is opaque to the ultrasound which might be transmitted/received in directions substantially deviating from normal to said transmitter/receiver surface 7 of the transmitter/receiver means 6, to consolidate the connection of the transmitter/receiver means 6 to cable 4, and to encase protect and hold said transmitter/receiver means 6 on the support means 8, while being implantable.

Perfect sealing can be obtained by fitting a thin sheath of silicone elastomer without fillers on the probe thus coated with silicone adhesive covering 10 immediately after the application of the latter. This sheath matches the general shape of the probe; its end is closed by holding it clamped during the setting of the adhesive. The use of a micro-thimble made of a silicone elastomer without fillers over the covering 10 is preferable. In both cases, the wall of the thimble or sheath situated in front of the probe surface 17 does not obstruct the passage of the ultrasound. Sealing will in any case be improved by reducing the number of contact surfaces of the various probe elements leading to the exterior at a line of contact.

Consequently, in a probe according to the invention, the sealing and electrical insulation means (not shown) are together formed by a thin sheath of implantable material which is transparent to ultrasound, more particularly made of a silicone elastomer without fillers, which covers and matches the outer shape of the support means 8, the silicone adhesive covering 10, and all or part of the cable 4, particularly the end near the transmitter/receiver means 6.

In the embodiments of the invention illustrated in the drawings, the support means 8 comprise an outer surface 17 to be applied to the organ 15 under exploration, said surface forming the transmission/receiving surface of the probe 1, the ultrasonic waves being transmitted from and received on said outer surface 17 as they are directed towards and come from the organ 15 under exploration, and an opposite inner surface 16 in contact with the transmitter/receiver means 6 and encased by the covering 10 so that the ultrasonic waves transmitted by the transmitting/receiving surface 7 of the transmitter/receiver means 6 at the opposite inner surface 16 pass through the support means 8 and then leave the probe via the outer surface 17 and, conversely, the waves originating from the organ enter the probe via the outer surface 17, pass through the support means 8 and are then picked up by the transmitting/receiving surface 7 of the transmitter/receiver means 6 as they leave the inner surface 16.

The ultrasonic waves must be transmitted at a certain angle to the direction of movement of the fluid whose speed is being measured (denoted by arrow F in FIG. 1). This angle of incidence is advantageously of the order of 60° in the case of an 8 MHz ultrasonic probe. Consequently, the transmitting/receiving surface 7 must also be inclined. However, calculation of this inclination must take into account Descartes' law of refraction and the different speeds of ultrasonic waves in the silicone elastomer and the fluid in question. Thus in a probe 1 according to the invention the opposite inner surface 16 of the support means 8 is inclined by an angle of the order of 20° with respect to the outer surface 17 of said support means 8, so that the ultrasonic waves penetrate at a direction indicated by arrow 31 into the organ under exploration at an appropriate angle, of 60° with respect to the direction of movement of the fluid whose speed is to be measured. The front surface 26 of the support means 8 covering 10 is so oriented as to be parallel to or diverge from the line 14 in the direction of transmission of the waves, thus ensuring that no transmitted or received beam is likely to strike against this wall.

The covering 10 advantageously line against the major part of the support means 8, only the outer surface 17 being left free for application to the organ 15 under examination, so that said covering forms a screen which is opaque to the ultrasound in the most effective way. In fact, the larger the covering 10, the less risk there will be of useless stray transmitted or received ultrasound and the better the accuracy of the information provided by the probe 1. In the embodiment of the invention illustrated in FIG. 2 of the drawings, the covering 10 does not completely overlie the flanks 18 of the support means 8, the covering 10 shown broken away in FIG. 2 for the sake of clarity. Preferably, however, the overlie 10 does cover these flanks 18 and, more generally, the cover 10 incases the investigation means 2 except for the outer transmission/reception surface 17. This improves sealing in addition to providing better acoustic insulation. The flanks 18 in the embodiment of FIG. 1 are advantageously inclined and form an angle of less than 90° with the outer surface 17. Said flanks 18 may even be tangential to the piezo-electric disc which forms the transmitter/receiver means 6. The front surface 26 may also form an angle very much less than 90° with the surface 17. The front wall may be an inclined semi-circular wall.

Figure 3:
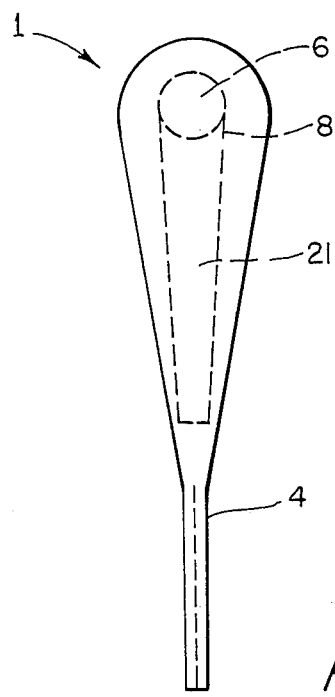
FIG. 3 is a plan view, on a reduced scale, of the probe of FIG. 1.

According to the invention the outer surface of the cover 10 is polished and as shown in FIG. 3, is substantially drop shaped, widening out progressively and continuously from that end of the cable 4 to which the transmitter/receiver means 6 is connected, to cover the trasmitter/receiver means 6, the electrical connection 13 of the lead 21 and 22 and the support means 8, except for the outer surface 17 which is applied to the organ 15 under investigation. This facilitates the removal without a complex surgical operation.

The probe 1 according to the invention advantageously comprises means (not shown) for rigid association with the organ 15 under exploration, thus obviating any subsequent accidental movement of the probe 1 when it is implanted, but still allowing subsequent removal. For example, said means providing rigid association on the organ 15 consist of a thin piece of implantable woven synthetic material adapted to be integrated with the organ 15 and rigidly associated with the probe, so as to be detachable in response to tension, the association being provided inter alia by gluing and so as to be tangential to the transmission/reception surface 17 of the probe, an opening being formed in said piece of synthetic material opposite to the transmission/reception surface 17 to allow the passage of the ultrasonic waves.

Also, the acoustic impedance Z1 of the piezo-electric transmitter/receiver means 6, which is generally made of ceramics, is very different from the acoustic impedance Z2 of the silicon elastomer support means 8. Consequently, the ultrasonic waves experience considerable interference as they pass from said transmitter/receiver means 6 into the support means 8, due to known phenomena, inter alia stray reflections. A probe 1 according to the invention therefore advantageously includes acoustic impedance matching means between the transmitter/receiver means 6 and the support means 8, inter alia to prevent stray reflections on the passage of the waves between the support means 8 and the transmitter/receiver means 6. Said impedance matching means comprise a layer of a material, which is preferably implantable, i.e. without any danger to the human or animal body, interposed between the transmitter/receiver means 6 and the support means 8. The acoustic impedance Z3 of this impedance matching means lies between the acoustic impedances Z1 and Z2 of the transmitter/receiver means 6 and of the support means 8, preferably in the region of the geometric mean of these impedances.

Conventionally, the acoustic impedance Z1 of the piezo-electric transmitter/receiver means 6 is of the order of 30 Pa.s/m, while the acoustic impedance Z2 of the support means 8 of silicone elastomer is of the order of 1 Pa.s/m. Thus the acoustic matching means will advantageously have an acoustic matching comprised between 3 and 10 Pa.s/m. inter alia of the order of 5 Pa.s/m.

The inventor has found that cold galvanization paints offer the properties required for making these acoustic impedance matching means. They can be sprayed in a thin layer, they are without risk to the organism, and have a satisfactory acoustic impedance. The acoustic impedance matching means are therefore preferably in the form of a thin layer of mixture sprayed on the transmitter/receiver surface 7 of the transmitter/receiver means 6. The thin sprayed layer is a coat of cold galvanization paint, for example one containing zinc and epoxy resins. This mixture sprays well and is not electrically conductive, thus obviating any short circuit or force contact problems with the electrical connections 13. It should be noted that this impedance matching coating reduces the natural frequency of the transmitter/receiver means 6, and this must be adapted accordingly.

The transmitter/receiver transducer means 6 advantageously comprise a disc of piezo-electric ceramics, preferably barium zirconate. For a probe transmission frequency of the order of 8 MHz, the diameter of this disc is about 4 mm and its thickness about 0.25 mm. Its surfaces are silvered to allow the electrical connections 13, as by soldering of the leads 21 and 21' of the coaxial cable 4 to said surfaces.

In order to obviate damage to said disc on application of the probe 1 to the organ 15, during manipulation or on its removal, the probe 1 advantageously comprises protection means 27, the object of which is to protect the transmitter/receiver means 6 and/or the means 9 for providing the rigid association between said transmitter/receiver means 6 and the support means 8 in order to prevent any damage to the means 6 and/or the rigid association thereof with the support means 8.

Said protection means 27 advantageously consists of a rigid element disposed above the piezo-electric disc 6, e.g. in the form of a cap, preferably without contact with said disc. The protection means 27 may be embedded in the covering 10, which, as above noted, engages the surface 24 of the piezo-electric disc 6.

Other embodiments can be considered, inter alia the application of a drop of plastic material 27 rigid enough to reinforce the piezo-electric disc forming the transmitter/receiver means 6, inter alia in its rear part having on it the connection 13. This drop, of shallow shape, should have its maximum thickness facing the rear edge of the disc 6 (weak point of the probe 1) and has no surface parallel to said disc 6. A synthetic resin such as polyester appears to be very suitable in view of its mechanical, acoustic and bio-compatible properties. An expanded rigid structure with non-communicating micro-bubbles would be perfect. The cover 10 may generally be a silicone adhesive which thus also additionally provides excellent sealing.

The means 9 for providing a rigid association between the transmitter/receiver means 6 and the support means 8 consist of a thin layer of glue, inter alia implantable (B) cyanoacrylate interposed between the inner surface 16 of the support means 8 and the impedance matching means, or the transmitter/receiver surface 7 of the transmitter/receiver means 6.

This layer of glue should be of the smallest thickness possible in order to avoid excessively modifying the frequency of the ultrasonic waves and in order to have an acoustic impedance mid-way between the acoustic impedance Z3 of the impedance matching means and the acoustic impedance Z2 of the support means 8, preferably in the region of the geometric mean of said impedances Z3 and Z2.

The cable 4 is usually of the coaxial type, but it may be two wires and twisted, this having been found advantageous in practice, inter alia in the case of external apparatus with a symmetrical input. Its leads are preferably made of split bare copper, or silver plated, and are soldered to the silver plated surfaces of the transmitter/receiver means 6. The cable 4 inter alia and preferably comprises a lead soldered to the transmitter/receiver surface 7 at 13, and a lead soldered at 13 to the surface 24 opposite the surface 7. In the latter case, the inner surface 16 of the support means 8 in contact with the transmitter/receiver means 6 advantageously has a groove 22 for the passage of the lead connected to surface 7; the latter may be rigidly associated with the support means 8, e.g. by gluing, by means of a drop of cyanoacrylate glue, inside groove 22, in order to hold the electrical connection 13 during handling of the probe 1. The cable 4 is protected over its entire length by a sheath 23 of implantable material, more particularly made of silicone elastomer with or without fillers. The socket is preferably a reversible miniature three-pin socket with gold-plated contacts.

Advantageously, the sheath 23 also covers the cover 10 and/or the support means 8 to form the sealing or electrical insulation means for the probe 1. In that case the probe 1 then has no outer contact line and is perfectly sealed and insulated electrically.

The support means 8 advantageously consists of a block of silicone elastomer without fillters, or any other implantable material which is a good conductor of ultrasound, forming a portion of a cylinder or cone the base of which forms the inner surface 16 and the outer surface 17 of said support means 8.

FIG. 1 illustrates a first embodiment of the invention in which the outer surface 17 for applying the support means 8 to the organ 15 under exploration is flat. However, in order to allow better matching of the probe to the organ 15, the outer application surface 17 preferably has a curved shape corresponding to the outer surface of said organ 15. More particularly, if the organ 15 is a blood vessel, the outer surface 17 is cylindrical concave, so as to match the outer shape of the organ 15 under exploration (see FIG. 2).

Two small side lugs 25 facilitate the fixing of the probe 1 on the organ 15, by the means for providing rigid association with the said organ, for example a resorbable thread, or in the manner indicated hereinbefore. The vessel enveloping angle should not be excessive, so as to allow for a certain diameter spread of the vessels being explored.

The transmission/reception surface 17 of the probe 1 should always be at an acute angle to a longitudinal line along the highest part of the cover 10 so as to be urged into in contact with the wall of the organ 15. The apex of this angle is directed towards the entry axis of cable 4 with the probe 1. Said surface 17 is inclined at the rear 30 so as to merge with the cover 10.

Silicone elastomer without fillers is a material which is relatively difficult to machine. It is therefore advantageous to machine, i.e., cut or mould the support means 8 from a block of silicone elastomer without fillers. In the case of cutting, the inner surface 16 and the outer surface 17 of the support means 8 are made polygonal. The shape resulting from the cutting or moulding should be as close as possible to spherical, this being the roundest possible, in order to facilitate installation and/or removal of the probe. It will be easier to give the outer surface of the cover 10 a drop shape if the support means 8 itself has a round shape.

In a method of producing a probe 1 according to the invention, the support means 8 is made inter alia by cutting or moulding from a silicone elastomer block, giving it the appropriate shape, and then rigidly associating the support means 8, inter alia by gluing, with the piezo-electric transmitter/receiver means 6, after the latter have been soldered to the output cable 4, whereupon the probe characteristics are tested (inter alia the frequency is measured), and if satisfactory (they are provided) the protection means 27 is fitted followed by a cover 10 to cover the transmitter/receiver means 6, the connections 13 with the output cable 4, the corresponding end 12 of said cable and the support means 8, except for the outer surface 17 (for application to the organ 15), and where provided the sealing means and/or electrical insulation such as a sheath or thimble is then fitted.

Figure 2:
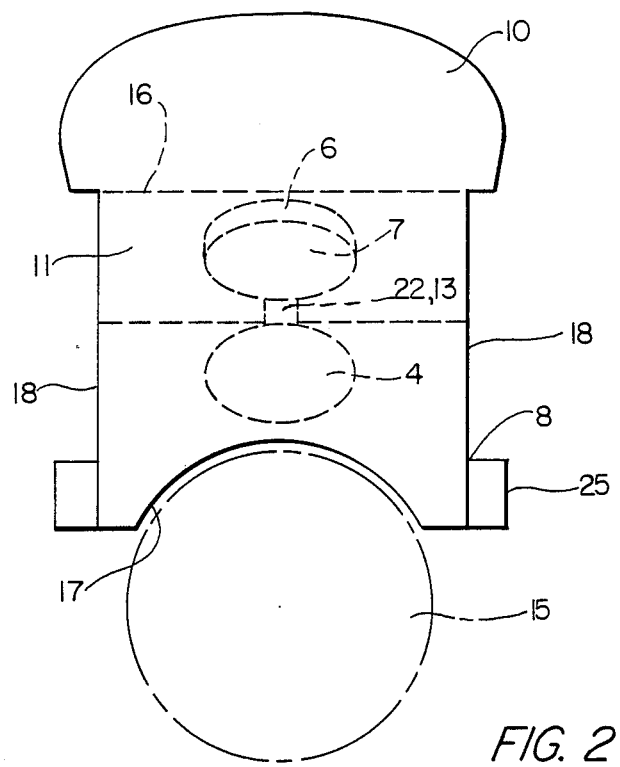
FIG. 2 is a diagrammatic front view (looking from the left in FIG. 1) of another embodiment of a probe according to the invention.

When the support means 8 has a concave outer surface 17 and/or lugs 25, as in the FIG. 2 embodiment it is necessary in practice to make it by moulding. In any case manufacturing it by moulding is advantageous because it reduces the production costs for the support means 8 while allowing more uniform manufacture thereof, the performance being more uniform, so that fewer probes have to be discarded during manufacture.

Preferably, the natural frequency Fo of the transmitter/receiver means 6 conncted to the cable 4 is measured and noted first of all, and then impedance matching means are placed on the transmitter/receiver means 6, inter alia on the transmitting/receiving surface 7. Before associating the piezo-electric transducer 6 with the support means 8, the natural frequency Fo' of the piezo-electric receiver/transmitter 6 is measured a second time: there should then be a frequency difference $F=Fo-Fo'$ of a certain value which must be complied with. In the case of a value found to be outside the tolerance, the coat of paint applied must be adjusted by additional spraying, scraping, or complete elimination by a solvent prior to restarting spraying completely.

In a method of making a probe according to the invention, transmitter/receiver means must be chosen which have a natural frequency above the frequency required for the ultrasonic waves for the investigations. In fact, the impedance matching means, and the means 9 for rigidly associating the transmitter/receiver means 6 with the support means 8 reduce the natural frequency of the transmitter/receiver means 6. Also, the frequency is adjusted by spraying an adequate impedance matching coating and associating the transmitter/receiver means 6 with the support means 8. It is the frequency variation which will indicate the thickness of the coating applied and hence its acoustic properties. The thickness of the glue used must also be taken into account in the choice of the transmitter/receiver means.

After the transmitter/receiver means have been associated with the support means 8, the frequency Fo" is measured a third time while noting the general slope of the impedance curve Z. This is a passive inspection, i.e. it is no longer possible to take any action to correct the characteristics of the resulting probe, unlike the second frequency measurement Fo'.

Before making the cover 10, it is desirable to carry out a test using the probe 1 as an ultrasound transmitter/receiver by means of an echo graph in mode A. The probe is then immersed in a container containing distilled water and a fixed target. The amplitude and the shape of the echo displayed by the echo graph completes the information given by the measurement of Fo". This echo graph inspection is essential in respect of the effectiveness of the probe 1 during manufacture: it may result in rejection of a probe which has satisfied the measurement of Fo" from the above-described impedance curve Z.

By way of example, a piezo-electric disc will be chosen of a diameter of about 4 mm and a thickness of 0.25 mm, which will have a natural frequency greater than 8 MHz. For example, assuming that this natural frequency is 8.41 MHz, (measured the first time), it must be reduced by about 0.25 MHz by the application of the impedance matching coating, by the application of coating between about 10 and 15 μm. Thus the transmission frequency of the ultrasonic waves of the finished probe 1 will be in the region of 8 MHz.

A probe 1 according to the invention is particularly suitable for repeated measurement of the blood velocity and rate of flow in a blood vessel in humans as necessary.

I claim:

1. A generally elongate ultrasonic transmitter/receiver probe adapted to be implanted in a human or animal body in contact with a vessel or a wall of an organ to allow exploration inside said organ by ultrasonics, the probe comprising:
   piezo-electric transmitter/receiver transducder means,
   support means for said transducer means having a first surface in operative juxtaposition to said transducer means and a second surface remote from said first surface for placement in contact with a vessel or a wall of an organ means for releasably attaching said probe to a vessel or organ,
   means including conductors extending from an end of said probe for connecting the transducer means with the outside of the body to carry information to and from said transducer means,
   means for encasing said transducer means and at least a portion of said support means but not said second surface, and a portion of said conductors adjacent to said transducer means and to said support means, the outer surface of said encasing means being polished and widening out progressively and continuously from adjacent said portion of said conductors and covering said transducer means and at least part of said support means, said conductors extending from said transducer means and support means in a direction substantially parallel to said second surface of said support means, whereby to allow the probe to be removed from the body by the pulling from outside on the conductors.

2. The probe of claim 1, wherein said support means is formed from an implantable material which is a good conductor of ultrasound, and the cover is formed from an implantable material which is opaque to ultrasound.

3. The probe of claim 1, wherein said support means is formed of a silicone elstomer without fillers and said cover is formed of silicone elastomer with fillers.

4. The probe of claim 1, and in combination therewith means for sealing the probe from surrounding fluids without interfering with the mechanical and acoustic characteristics thereof and for electrically insulating the conductors and the transducer means comprising a thin sheath of implantable material covering said probe and at least part of said conductors.

5. The combination of claim 4, said thin sheath being of silicone elastomer without fillers.

6. The probe of claim 1, and further comprising acoustic impedance matching means on the transmitting/receiving surface means of said transducer means comprising means for preventing stray reflections upon the passage of ultrasonic waves between the support means and the transducer means.

7. The probe of claim 6, wherein said acoustic impedance matching means is a coat of cold galvanization paint.

8. The probe of claim 7, wherein said paint contains zinc and epoxy resins.

9. The probe of claim 1, and further comprising means overlying said transducer means for resisting mechanical forces on said transducer means when the probe is handled, whereby to diminish the risk of breakage thereof.

10. The probe of claim 9, wherein said transducer means has an edge which is closest to the portion of said probe into which said conductors enter, and said last mentioned means comprising rigid plastic material having a maximum thickness adjacent the said edge.

11. The probe of claim 1, and further comprising a sheath of implantable material over said conductors, said sheath extending over at least one of said covering means and said support means, said sheath forming sealing and electrical insulating means for said probe.

12. The probe of claim 1, said conductors comprising two twisted wires.

13. The probe of claim 1, wherein said support means is in the form of a prism, and said first and second surfaces form bases of said prism.

14. The probe of claim 1, said support means further comprising a front surface of said flanks, at least one thereof being inclined and forming an angle of less than 90° with said second surface of said support means.

15. The probe of claim 1, wherein said support means comprises a front surface and flanks, at least one of which is tangential to said transducer means.

16. The probe of claim 1, wherein said second surface of said support means is substantially flat.

17. The probe of claim 1, wherein said second surface of said support means is cylindrically concave.

18. The probe of claim 1, said attaching means comprising side lugs extending outwardly for attaching the probe to an organ by threads engaging said lugs.

19. The probe of claim 1, wherein said first surface of said support means is inclined at an angle of approximately 20° relative to said second surface of said support means, so that ultrasonic waves are directed into an organ to which said probe is attached at an angle of approximately 60° with respect to the direction of movement of fluid in said organ.

20. The probe of claim 1, said second surface of said support means being at an acute angle to a longitudinal line along the highest part of said covering means with the apex of said angle directed toward the entry axis of said conductors, whereby to urge said second surface into contact with the wall of an organ, the rear part of said second surface merging with said cover means.

21. The method of manufacturing an ultrasonic probe comprising:
   (a) providing transducer means;
   (b) providing linear electrical conductors and attaching said conductors to said transducer means, measuring the natural frequency of said transducer means, and then applying impedance matching means to said transducer means, and again measuring the natural frequency of said transducer means and the applied impedance matching means;
   (c) providing thereafter a block of material which is a good conductor of ultrasound;
   (d) rigidly attaching said block to a surface of said transducer means whereby to form an ultrasonic probe;

(e) testing said probe to determine the frequency thereof;

(f) encasing with a covering said transducer means, the attachments of said transducer means to said conductors, a portion of said conductors adjacent to said transducer means, and a substantial portion of said block other than a surface thereof remote said transducer means.

22. The method of claim 21, and further comprising adjusting the frequency of an electro-mechanical probe by applying an impedance matching coating to said transducer means.

23. A method for utilizing an ultrasonic probe for measuring the flow of fluid in an organ comprising:

(a) providing a generally elongate ultrasonic probe including a transducer, a support for said transducer having a transmitting/receiving surface for engaging an organ, and conductor means attached to said transducer means and extending from an end of said elongate probe, and further comprising an encasing cover for said transducer means, for portions of said support other than said transmitting/receiving surface, and for the portions of said conductor means adjacent to said transducer means and said support, the outer surface of said encasing cover being polished and widening out progressively and continuously from adjacent said portion of said conductor means and encasing said transducer and at least said portions of said support means;

(b) implanting said probe means in a body with said transmitting/receiving surface adjacent and in engagement with an organ, and with said conductor means extending exteriorly of said body;

(c) measuring characteristics of said body by use of said probe; and (d) removing said probe from said body by pulliing on said conductor means.

24. A generally elongate ultrasonic transmitter/receiver probe adapted to be implanted in a human or animal body, intended for application in contact with a vessel or a wall of an organ to allow exploration inside said organ by ultrasonics, the probe comprising:

piezo-electric transmitter/receiver transducer means, support means for said transducer means having a first surface in operative juxtaposition to said transducer means and a second surface remote from said first surface for placement in contact with a wall of an organ, said support means being formed from an implantable material which is a good conductor of ultrasound, means for releasably attaching said probe to a vessel or organ means including conductors for connecting the transducer means with the outside of the body to carry information to and from said transducer means and being substantially parallel to said second surface, means for encasing said transducer means and at least a portion of said support means but not said second surface, and a portion of said conductors adjacent to said transducer means and said support means, said encasing means formed from an implantable material opaque to ultrasound.

25. The probe of claim 24, wherein said support means is formed of a silicone elastomer without fillers and said cover is formed of silicone elastomer with fillers.

* * * * *